United States Patent [19]

Klinkmann et al.

[11] 4,260,827

[45] Apr. 7, 1981

[54] PROCESS FOR THE PURIFICATION OF AQUEOUS SOLUTIONS OF LOW MOLECULAR WEIGHT POLYHYDROXYL COMPOUNDS

[75] Inventors: Kurt Klinkmann; Raimund Wambach, both of Leverkusen, Fed. Rep. of Germany

[73] Assignee: Bayer Aktiengesellschaft, Leverkusen, Fed. Rep. of Germany

[21] Appl. No.: 104,406

[22] Filed: Dec. 17, 1979

[30] Foreign Application Priority Data

Dec. 20, 1978 [DE] Fed. Rep. of Germany ....... 2855038

[51] Int. Cl.³ ....................... C07C 27/26; C07C 29/74
[52] U.S. Cl. ...................................... 568/414; 203/38; 203/41; 203/66; 568/497; 568/872; 210/664; 210/668; 210/687; 210/688
[58] Field of Search ............... 568/870, 872, 414, 497; 210/54, 26, 28, 38 R, 38 A, 38 B; 203/38, 63, 66, 39, 41

[56] References Cited

U.S. PATENT DOCUMENTS

| | | | |
|---|---|---|---|
| 3,040,104 | 6/1962 | Sarappo et al. | 568/872 |
| 3,134,814 | 5/1964 | Sargent et al. | 568/872 |
| 3,315,002 | 4/1967 | Small | 568/872 |
| 3,778,368 | 12/1973 | Nakamura et al. | 210/54 R |
| 4,062,900 | 12/1977 | Tanabe et al. | 568/872 |

*Primary Examiner*—Frank Sever
*Attorney, Agent, or Firm*—Gene Harsh; Joseph C. Gil

[57] ABSTRACT

The invention is directed to a process for the purification of aqueous solutions of low molecular weight polyhydroxyl compounds containing calcium or lead compounds or mixtures thereof. Methanol and a precipitant for calcium and/or lead ions in a quantity equivalent to the ions to be removed are added to the solutions. The deposits thus formed are removed and the residual solutions are treated with a cation exchanger followed by distillation of the low-boiling fractions. The distillation sump which essentially contains the low molecular weight polyhydroxyl compounds is then treated with an anion exchanger.

2 Claims, No Drawings

PROCESS FOR THE PURIFICATION OF AQUEOUS SOLUTIONS OF LOW MOLECULAR WEIGHT POLYHYDROXYL COMPOUNDS

BACKGROUND OF THE INVENTION

The invention relates to a process for the purification of aqueous solutions of low molecular weight polyhydroxyl compounds. It is known that low molecular weight polyhydroxyl compounds can be obtained by condensing formaldehyde in the presence of lead compounds (German Offenlegungsschrifts Nos. 2,714,084 and 2,721,186 corresponding substantially to U.S. Application Ser. Nos. 829,171; 829,167 and 829,173 all filed on Aug. 30, 1977) or calcium compounds (German Offenlegungsschrift No. 2,721,186 substantially corresponding to U.S. Application Ser. No. 829,173).

Low molecular weight polyhydroxyl compounds, which may be hydrogenated to reduce carbonyl groups to hydroxyl groups, are valuable chain extenders and crosslinkers for polyurethane plastics as described in U.S. Application Ser. Nos. 829,171 and 829,167. In addition, they may be converted into non-ionic surface-active compounds by esterification with long-chain aliphatic monocarboxylic acids or by ethoxylation, as described in K. Lindner's "Tenside", Vol. III, Wissenschaftliche Verlagsgesellschaft Stuttgart 1964, page 2336.

The processes described above require purified low molecular weight polyhydroxyl compounds. For example, calcium and/or lead compounds, which are present in the solutions of low molecular weight polyhydroxyl compounds from the process used for their production must be removed after the formaldehyde condensation and before or after the optional hydrogenation step.

It is known that low molecular weight polyhydroxyl compounds can be freed from lead compounds by precipitation in sulfate form using sulfuric acid (U.S. Application Ser. Nos. 829,171 and 829,167).

DESCRIPTION OF THE INVENTION

It has now been found that aqueous solutions of low molecular weight polyhydroxyl compounds containing calcium or lead compounds, or a mixture of calcium and lead compounds, can be purified by removing the calcium and/or lead compounds using the following process. Methanol is added to the solutions and a precipitant is added in a quantity equivalent to the amount of ions to be removed. The deposit thus formed is separated off and the residual solution is treated with a cation exchanger. The low-boiling fractions are distilled off after separation from the cation exchanger and the distillation sump, which essentially contains the low molecular weight polyhydroxyl compounds, is treated with an anion exchanger.

Examples of aqueous solutions of low molecular weight polyhydroxyl compounds include solutions containing from 10 to 80% by weight, preferably from 40 to 75% by weight of low molecular weight polyhydroxyl compounds containing from 2 to 10, preferably from 2 to 6 carbon atoms. Such aqueous solutions of polyhydroxyl compounds also contain from 0.005 to 5% by weight, preferably from 0.01 to 1% by weight of calcium and/or lead ions.

The quantity of methanol added to the aqueous solution of the low molecular weight polyhydroxyl compounds may range from 20 to 300% by weight, preferably from 100 to 200% by weight of the total weight of the aqueous solution.

The calcium and/or lead compounds present in the solution of the low molecular weight polyhydroxyl compounds are then precipitated by the addition of an equivalent quantity of precipitant for calcium and/or lead ions. Suitable precipitants are compounds, which with the calcium and/or lead compounds present, form substantially insoluble deposits, such as phosphates, oxalates or sulfates. It is preferred to use precipitants which form sulfates as the substantially insoluble deposits.

In order to maximize precipitation of the calcium and/or lead compounds, it is possible to adjust the pH-value of the solution of low molecular weight polyhydroxyl compounds to from 1 to 4 and preferably from 2 to 3. To obtain phosphates, oxalates or sulfates for example, the corresponding acids, such as orthophosphoric acid, oxalic acid or sulfuric acid may be used as the precipitant. It is preferred to use sulfuric acid. The acids may be used in concentrated or dilute aqueous form.

After the deposit formed by the precipitant has been removed, for example by filtration, the solution of the low molecular weight polyhydroxyl compounds is treated with a cation exchanger. Suitable cation exchangers include, for example, synthetic exchangers based on Bakelite- or aminoplast-like condensation resins, or crosslinked polymerization resins such as crosslinked polystyrene, which may contain for example sulfonic acid, phosphonic acid or carboxylic acid groups (Houben-Weyl, Methoden der Organischen Chemie, Vol. 1/1, Georg Thieme Verlag, Stuttgart 1958, pages 527 to 529).

After the solution of the low molecular weight polyhydroxyl compounds has been separated from the cation exchanger, the low-boiling fractions are distilled off from the solution. The low-boiling fractions include, for example, some of the methanol added in the process or low-boiling fractions which are formed during the process, optionally in contact with the cation exchanger, such as formic acid methyl ester. During the distillation of the low-boiling fractions, it is possible to collect a quantity of distillate of from 2 to 15% by volume, preferably from 4 to 10% by volume, based on the volume of the methanol used.

After the low-boiling fractions have been distilled off, the solution of the low molecular weight polyhydroxyl compounds is treated with an anion exchanger. Suitable anion exchangers include for example, synthetic exchangers based on Bakelite- or aminoplast-like condensation resins, or crosslinked polymerization resins such as crosslinked polystyrene, which may contain for example amino groups, imino groups or quaternary ammonium groups (Houben-Weyl, Methoden der Organischen Chemie, Vol. 1/1, Georg Thieme Verlag, Stuttgart 1958, pages 527–529).

The treatment of the solution of the low molecular weight polyhydroxyl compounds with the cation exchanger and the anion exchanger may be carried out by stirring the granulated exchanger into the solution or by passing the solution through a column filled with the exchanger. It is preferred to use the column process.

The treatment of the solution of the low molecular weight polyhydroxyl compounds with the cation exchanger and the anion exchanger may be carried out at a temperature of from 0° to 70° C., preferably at a temperature of from 20° to 40° C.

The process may be carried out as follows.

Methanol is added to the solution of the low molecular weight polyhydroxyl compounds, followed by the addition with stirring of a precipitant in a quantity equivalent to the ions to be removed. The deposit formed is then filtered off and the filtrate is passed through a column filled with a cation exchanger. The solution from the cation exchange column is then heated to a temperature of from 60° to 70° C. in a distillation apparatus until about 5 to 15% by volume of distillate, based on the volume of the methanol added to the starting solution, has accumulated. The distillation sump is cooled to around 30° to 40° C. and then passed through a column filled with an anion exchanger. The deionized solution of low molecular weight polyhydroxyl compounds is collected from the anion exchanger.

The process permits solutions of low molecular weight polyhydroxyl compounds to be extensively deionized. The degree of deionization is greater than that obtainable by conventional processes, such as the mere precipitation of the ions in the form of insoluble salts or the deposition of ionic compounds with methanol. Thus, the solubility of calcium sulfate and lead sulfate in solutions of low molecular weight polyhydroxyl compounds is relatively high. 1 liter of aqueous solution containing approximately 60% by weight of low molecular weight polyhydroxyl compounds merely precipitated with sulfuric acid and filtered, still contains around 1600 ppm of calcium and around 27 ppm of lead starting from any higher concentration. However, the aqueous solutions of low molecular weight polyhydroxyl compounds initially containing from 0.005 to 5%, preferably from 0.01 to 1% by weight of calcium and/or lead ions purified by the process of the invention contain less than 5 ppm and preferably less than 2 ppm of calcium ions and/or less than 1 ppm and preferably less than 0.5 ppm of lead ions.

Additionally, the precipitation of inorganic cations in the form of substantially insoluble salts from solutions of low molecular weight polyhydroxyl compounds by the addition of methanol is unsatisfactory because the solutions contain formic acid from the formaldehyde condensation. The lead formate for example remains significantly soluble, even where methanol is added.

Deionization by ion exchangers alone would require uneconomically large ion exchange units. If smaller ion exchange units were used, the exchange resins would have to be regenerated frequently because of the high ion concentration of solutions produced by the condensation of formaldehyde in the presence of calcium or lead salts. Additionally, the solutions of polyhydroxyl compounds would be undesirably diluted due to the necessary washing out of polyhydroxyl compounds adhering to the resin. In addition, frequent regeneration would result in the accumulation of large quantities of effluent. Moreover, the formic acid generated from the formaldehyde condensation would saturate the anion exchangers of an ion exchanger unit very quickly.

It is surprising that the invention provides for greater deionization than might have been expected from the combination of the conventional processes described above. It is also surprising that the formic acid present in the solutions of low molecular weight polyhydroxyl compounds can be esterified with methanol even though the solutions contain large molar excesses of water. Thus, surprisingly the formic acid can be removed in the form of methyl formate so that the formic acid does not saturate the anion exchanger too quickly.

EXAMPLES

Example 1 (Comparison Example)

600 ml of 20.1% by weight sulfuric acid are added while stirring at room temperature to 10 kg of an aqueous solution containing 58.6% by weight of low molecular weight polyhydroxyl compounds and 7000 ppm of calcium ions, 860 ppm of lead (II) ions and 1.27% by weight of formate ions. The rest of the solution is water. The solution is filtered off from the deposit formed. 176 g of filter residue are obtained. The filtrate was found to contain 1600 ppm of calcium ions, 27 ppm of lead ions, 1.12% by weight of formate ions and 0.32% by weight of sulfate ions.

Example 2 (Comparison Example)

1830 g of ethylene glycol and then 600 ml of 20.1% by weight sulfuric acid are added while stirring at room temperature to 10 kg of the aqueous solution described in Example 1. The deposit formed is filtered from the solution. 191 g of filter residue are obtained. The filtrate was found to contain 1100 ppm of calcium ions, 25 ppm of lead ions, 0.86% by weight of formate ions and 0.22% by weight of sulfate ions.

Example 3 (According to the invention)

15 kg of methanol and then 600 ml of 20.1% by weight sulfuric acid are added while stirring at room temperature to 10 kg of the solution described in Example 1. The deposit formed is filtered from the solution. A filter residue of 232 q is obtained. The filtrate was found to contain 41 ppm of calcium ions, 5.0 ppm of lead ions, 0.24% by weight of formate ions and 0.032% by weight of sulfate ions.

Example 4 (Comparison Example)

600 g of methanol, 24.1 g of basic lead carbonate (containing 19.28 g of lead) and 6 g of formic acid are added to 1 kg of fully demineralized aqueous solution containing 60% by weight of low molecular weight polyhydroxyl compounds. This mixture is stirred for 2 hours at 70° C. and then filtered. The clear filtrate was found to contain a lead total of 17.485 g. The filtrate is freed from water and methanol by vacuum distillation. The clear, pale yellow residue has a total lead content of 17.1 g. The residue is dissolved twice in twice the quantity of methanol by weight and reconcentrated by evaporation each time. No lead formate precipitated from the methanolic solutions. Finally, the mixture of low molecular weight polyhydroxyl compounds was still found to contain 16.8 g of lead. The difference between the quantity of lead introduced (17.485 g) and the quantity of lead finally detected (16.8 g) was removed with the analysis samples.

Example 5

The quantities of methanol indicated in Table 1 are added to batches of 1000 g of an aqueous solution containing 60% by weight of low molecular polyhydroxyl compounds and 0.7% by weight of formic acid, after which the solutions were passed through a column filld with a strongly acid cation exchanger. Table 1 shows the respective formic acid contents determined by titration before and after the cation exchanger.

TABLE 1

| Solution of the low molecular weight polyhydroxyl compounds g | Methanol Added g | Formic Acid Content | |
| --- | --- | --- | --- |
| | | Before the Exchanger % | After the Exchanger % |
| 1,000 | 200 | 0.58 | 0.213 |
| 1,000 | 400 | 0.516 | 0.183 |
| 1,000 | 600 | 0.459 | 0.136 |
| 1,000 | 1,000 | 0.364 | 0.119 |
| 1,000 | 1,300 | 0.318 | 0.072 |
| 1,000 | 1,600 | 0.29 | 0.055 |
| 1,000 | 1,900 | 0.26 | 0.040 |

Example 6

Batches of 1000 g of the same solution as in Example 5, except that they each have a formic acid content of 3.4% by weight, are treated in the same way as described in Example 5. The results are set out in Table 2.

TABLE 2

| Solution of the low molecular weight polyhydroxyl compounds g | Methanol Added g | Formic Acid Content | |
| --- | --- | --- | --- |
| | | Before the Exchanger % | After the Exchanger % |
| 1,000 | 200 | 2.79 | 0.694 |
| 1,000 | 400 | 2.36 | 0.637 |
| 1,000 | 600 | 2.0 | 0.373 |
| 1,000 | 1,000 | 1.7 | 0.274 |
| 1,000 | 1,300 | 1.4 | 0.185 |
| 1,000 | 1,600 | 1.3 | 0.168 |
| 1,000 | 1,900 | 1.2 | 0.150 |

Example 7

5000 g of methanol are added while stirring at room temperature to 2500 g of an aqueous solution containing 1500 g (60.0% by weight) of low molecular weight polyhydroxyl compounds, 7226 mg of calcium ions, 83 mg of lead (II) ions and 16.2 g of formate ions. 78 ml of 20% by weight sulfuric acid are then added to this solution, again while stirring at room temperature. The deposit precipitated is filtered off under suction, leaving 30 g of filter residue of which the analysis shows a content of 21.4% by weight of calcium 2.4% by weight of lead and 53.1% by weight of sulfate ions. The filtrate contains 130 ppm of calcium ions, 750 ppb of lead (II) ions, 0.013% by weight of sulfate ions and 0.18% by weight of formate ions. The filtrate is then passed at a rate of 11.7 liters per hour at room temperature through a chromatography column containing 41 liters of a strongly acid cation exchanger (containing sulfonic acid groups) based on a polystyrene crosslinked with divinyl benzene. The effluent from this chromatography column contains 1 ppm of calcium ions, less than 50 ppb of lead (II) ions, 0.015% by weight of sulfate ions and 0.02% by weight of formate ions.

The solution obtained as effluent is heated to around 65° C. in a distillation apparatus, the distillate being collected in a quantity which corresponds to 10% of the quantity of methanol indicated above.

The distillation residue is then cooled to around 35° C. Its analysis shows 1 ppm of calcium ions, less than 50 ppb of lead (II) ions, 0.015% by weight of sulfate ions and less than 0.02% by weight of formate ions. The distillation residue is then passed at a rate of 0.65 liters per hour at 35° C. through a chromatography column filld with 1 liter of a macroporous weakly basic anion exchanger (containing amino groups) based on a polystyrene crosslinked with divinyl benzene. The effluent from the chromatography column with the anion exchanger contains 1 ppm of calcium ions, less than 50 ppb of lead (II) ions, 0.06% by weight of sulfate ions and no detectable quantities of formate ions.

What is claimed is:

1. A process for the purification of aqueous solutions of low molecular weight polyhydroxyl compounds containing calcium or lead compounds or a mixture of calcium and lead compounds by removing calcium and/or lead compounds comprising:

(a) adding from about 20–300 wt. percent methanol to said solutions, (b) adding a precipitant for calcium and/or lead compounds to said solutions in a quantity equivalent to the ions to be removed, (c) separating from the solutions the deposits formed by steps (a) and (b), (d) treating the residual solutions with a cation exchanger, (e) distilling off low-boiling fractions from said residual solutions after separation from the cation exchanger, and (f) treating the distillation sump essentially containing the low molecular weight polyhydroxyl compounds with an anion exchanger.

2. The process of claim 1 in which the pH of said aqueous solutions is adjusted to a value of from 1 to 4.

* * * * *